US00PP34662P2

(12) United States Plant Patent
Berry

(10) Patent No.: US PP34,662 P2
(45) Date of Patent: Oct. 18, 2022

(54) ***HIBISCUS* PLANT NAMED 'JBG RH-05'**

(50) Latin Name: *Hibiscus rosa-sinensis*
Varietal Denomination: JBG RH-05

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/803,119

(22) Filed: Feb. 17, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257

CPC ... A01H 5/02; A01H 5/00; A01H 6/60; A01H 6/608

See application file for complete search history.

(56) References Cited

PUBLICATIONS

Monrovia 2022 Distinctive Selections, retrieved on Mar. 21, 2022, retrieved from the Internet at https://f.hubspotusercontent20.net/hubfs/1925176/2022%20DistinctiveSelectionsGuide_FINAL.pdf, 2 introductory pages and p. 15. (Year: 2022).*

Sparks Highlights from Cultivate'20 Virtual: New Products and New Educational Opportunities, Greenhouse Grower, retrieved on Mar. 21, 2022, retrieved from the Internet at https://www.greenhousegrower.com/management/highlights-from-cultivate20-virtual-new-products-and-new-educational-opportunities/, 7 pp. (Year: 2020).*

* cited by examiner

*Primary Examiner* — June Hwu
(74) *Attorney, Agent, or Firm* — The Webb Law Firm

(57) ABSTRACT

A new and distinct *Hibiscus* plant having primarily soft apricot orange colored flowers without an eye present.

2 Drawing Sheets

Botanical classification: *Hibiscus rosa-sinensis.*
Varietal denomination: 'JBG RH-05'.

BACKGROUND OF THE INVENTION

The present invention comprises a new and distinct *Hibiscus* plant having the varietal name 'JBG RH-05'. The new variety is the result of a planned breeding program with the purposes of developing *Hibiscus rosa-sinensis* plants that exhibit whitefly and leaf spot resistance, propagation and production efficiencies, durable and exotic flowers, and abundant flowering. 'JBG RH-05' is the result of a cross conducted in Grand Saline, Tex. between *Hibiscus rosa-sinensis* varieties 'JBG 15010' (female parent, unpatented) and 'JBG 14007' (male parent, U.S. Plant Pat. No. 31,302). The new variety was selected in February of 2016 in Grand Saline, Tex. and the first asexual reproduction of the new variety was conducted by semi-hardwood cuttings in June of 2016 in Grand Saline, Tex. 'JBG RH-05' has been trial and field tested and has been found to retain its distinctive characteristics and remain true to type through successive propagations. The present invention has not been evaluated under all possible environmental conditions. However, it has been found to thrive in production and adapt well to the environment in Homestead, Florida. The phenotype may vary with variations in environment without a change in the genotype of the plant.

'JBG RH-05' is similar to its female parent in leaf color and having orange-toned flower petals. 'JBG RH-05' differs from its female parent in having slightly smaller and more durable flowers. 'JBG RH-05' is similar to its male parent in having a moderately vigorous growth rate. 'JBG RH-05' differs from its male parent in flower color, having overlapping flower petals, and the absence of a flower eye.

When 'JBG RH-05' is compared to *Hibiscus rosa-sinensis* variety having a commercial name of "Best Friend" (unpatented), both varieties have a main flower color of orange and similar foliage color. However, 'JBG RH-05' has larger flowers and more vigorous and less compact growth than "Best Friend".

The following traits distinguish 'JBG RH-05' as a new and distinct cultivar from other *Hibiscus* varieties known to the breeder:

1. Flower color that starts as orange/pink and bleeds outward to a soft apricot orange color;
2. Dense branching with a mounding habit; and
3. Lack of a flower eye.

DESCRIPTION OF THE DRAWINGS

The accompanying photographic images illustrate the new variety at approximately three years of age, with the colors being as nearly true as is possible with color illustrations of this type.

DESCRIPTION OF THE PLANT

Figure 1:
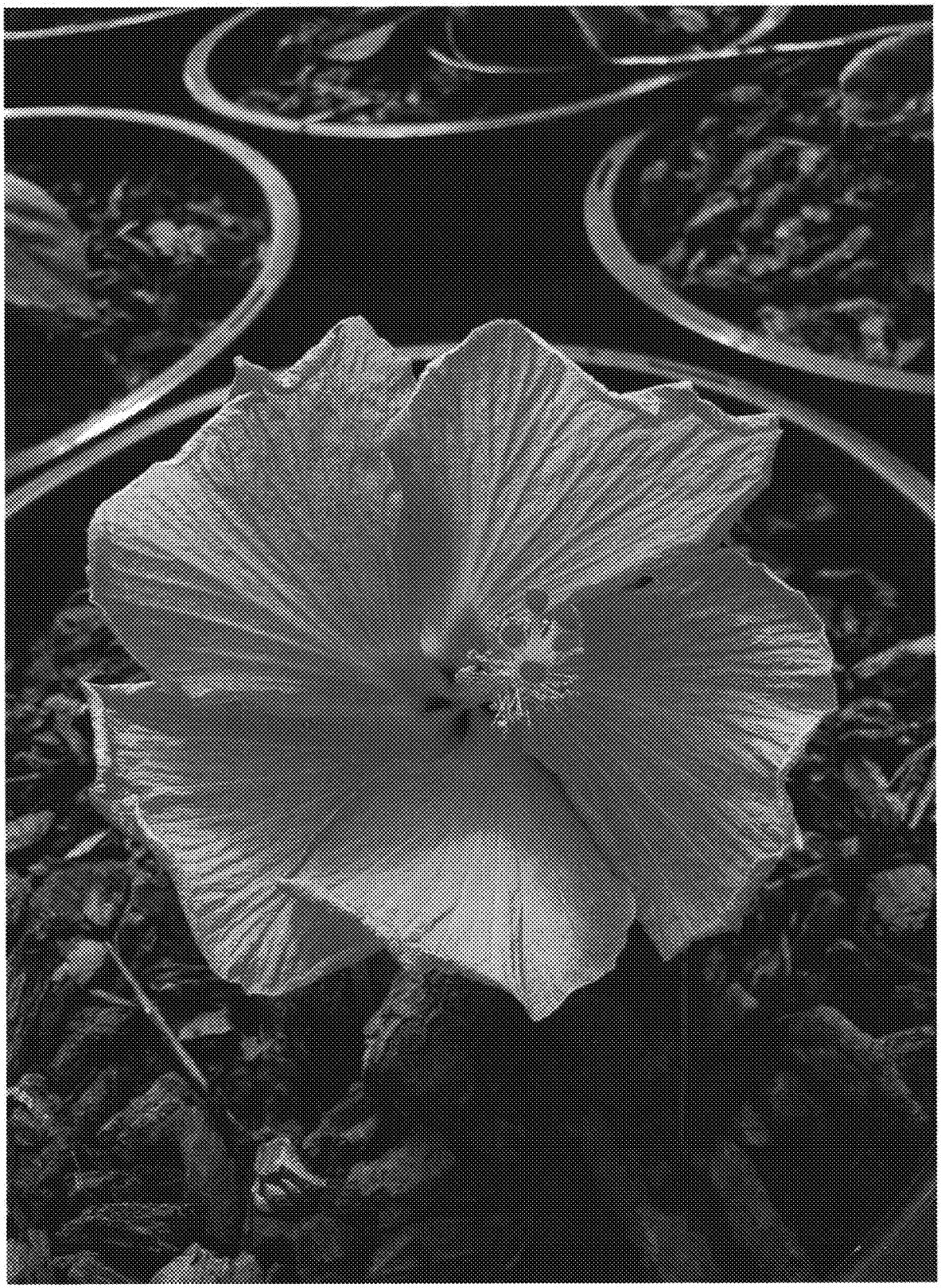
FIG. 1 illustrates a close-up view of a flower of the new variety.
Figure 2:
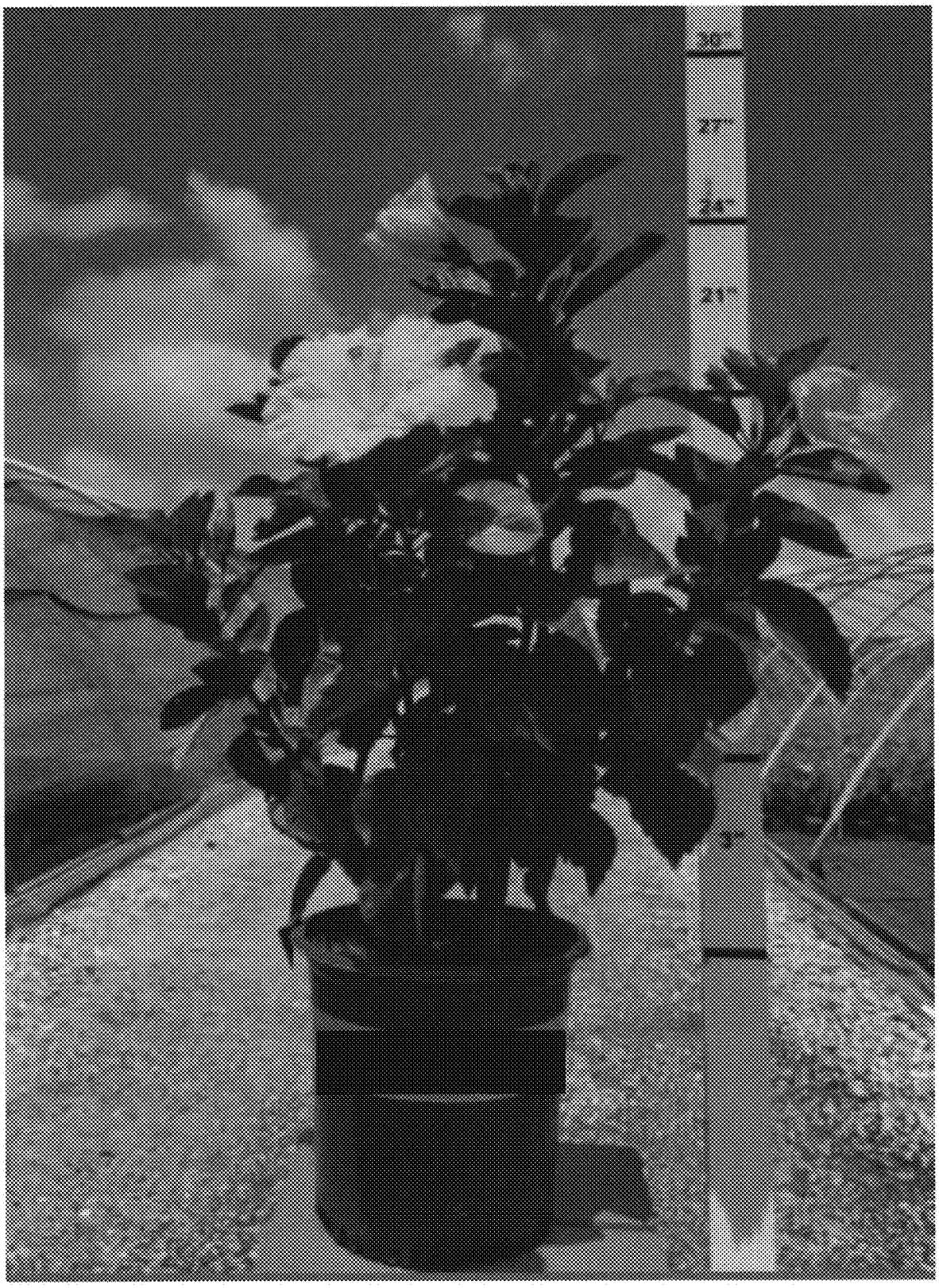
FIG. 2 illustrates a close-up view of an entire plant of the new variety.

The following detailed description sets forth the characteristics of the new variety. The plants were grown in a greenhouse with bottom heat in boxed, 1 yard soil containers. The color readings and measurements were taken indoors under natural light in a greenhouse on approximately three year old plants. Color references are primarily to the Munsell Color Chart (accessed online in 2022), except where general color terms are used.

PLANT

Time to initiate roots: About 12 days at an average of 24° C.
Time to develop roots: About 50 days at an average of 21-24° C.
Time to produce a finished flowering plant from a rooted cutting: About 12-16 weeks in a 1 gallon/20.0 cm diameter container.
Specific disease/pest resistance: Resistance to whitefly (*Trialeurodes vaporariorum*) and bacterial leaf spot (*Pseudomonas* spp.).
Heat/cold tolerance: Thrives above 13° C., but expires at temperatures of 0° C. and below.
Drought tolerance: Moderate to none.
Plant:
*Type*.—Tropical, ornamental shrub.
*Habit*.—Bush-like.
*Height*.—1.5 m.
*Spread*.—1.5 m.
*Vigor*.—Moderate.
*Rooting*.—Coarse and well-branched.
Stem:
*Number per plant*.—15.
*Length*.—61.0 cm.
*Width*.—1.3 cm.
*Texture*.—Immature: Smooth, green, semi-hard wood. Mature: Medium-textured, brown, hard wood.
*Strength*.—Moderate and flexible.
*Branch arrangement*.—Alternate.
*Internode length*.—3.8-5.1 cm.
*Color*.—Immature: 10GY 5/8. Mature: 10YR 2/6.
*Stipules*.—Number per node: 2. Shape: Pointed. Length: 0.6 cm. Width: 1.6 mm Surface texture: Smooth. Apex: Acute. Base: Attached. Margin: Entire. Color: 10GY 5/8.
Foliage:
*Arrangement*.—Alternate.
*Size of leaf*.—Length: 15.2 cm. Width: 14.0 cm.
*Shape of leaf* (*generally*).—Cordate/oval.
*Shape of apex*.—Mucronate/cuspidate.
*Shape of base*.—Rounded/cordate.
*Texture*.—Upper surface: Semi-abrasive and shiny. Lower surface: Semi-abrasive.
*Margin type*.—Slightly serrate.
*Color*.—Young leaves: Upper surface: 10GY 4/10. Lower surface: 10GY 6/10. Mature leaves: Upper surface: 10GY 4/10. Lower surface: 10GY 6/10.
*Veins*.—Venation type: Netted. Color: Upper surface: 5GY 7/8. Lower surface: 5GY 7/8.
*Petiole*.—Length: 5.1 cm. Diameter: 3.2 mm. Texture: Smooth. Color: 10GY 5/8.

FLOWERS

Buds (described in a tight/not swollen/not opened state):
*Shape*.—Urn.
*Diameter*.—1.3 cm.
*Length*.—3.2 cm.
*Color*.—10GY 6/10, but 10YR 8/20 when pushing color/swollen/not yet opened.
Natural flowering season: May to October in Azusa, Calif.
Flower type and habit: Complete and single.
Fragrance: Mild floral.
Flowers:
*Number per stem*.—1-7.
*Overall depth*.—12.7 cm.
*Overall diameter*.—20.3 cm.
*Shape*.—Stellate.
*Lastingness*.—1-3 days on the plant.
*Petals*.—Number: 5. Arrangement: Open and overlapping. Length: 10.2 cm. Width: 7.6 cm. Shape: Oblanceolate. Apex: Round, with incisions absent. Base: Acute. Margin: Entire, with weak undulation intensity. Texture/appearance: Upper surface: Soft and smooth. Lower surface: Semi-abrasive. Color: When opening: Upper surface: 5YR 7/8. Lower surface: 5YR 6/8. Fully opened: Upper surface: 5YR 7/8 with a ring of transitioned 5YR 6/8 and a 10YR 8/8 center. Lower surface: 5YR 6/8.
*Calyx*.—Form: Free. Overall length: 2.5 cm. Overall diameter: 2.5 cm. Sepals/calyx lobes: Number: 7. Shape: Pointed. Apex: Pointed. Margin: Entire. Texture: Semi-abrasive. Color: Outer surface: 10GY 5/8. Inner surface: 10GY 6/10.
*Epicalyx*.—Average number: 6 per flower. Length: Fused at base-2.5 cm. Width: 2.5 cm. Texture: Semi-abrasive. Color: 10GY 6/10.
*Bracts*.—Location: Part of the epicalyx — encircling the true calyx at the base of the sepals. Number: 2. Position: Opposite. Length: 0.6 cm. Width: 1.6 mm Shape: Pointed. Apex: Pointed. Base: Attached. Margin: Entire. Texture/appearance: Upper surface: Semi-abrasive. Lower surface: Semi-abrasive. Color: Outer surface: 10GY 6/10. Inner surface: 10GY 6/10.
*Peduncle*.—Length: 8.9 cm. Diameter: 3.2 mm Strength: Strong. Angle: 45°. Texture: Smooth. Color: 10GY 6/10.
Reproductive organs:
*Gynoecium*.—Pistils: Number: 1. Length: 8.9 cm. Stigma: Number: 5. Shape: Round. Length: 3.2 mm. Diameter: 3.2 mm. Color: 5R 4/14. Style: Length: 0.6 cm. Width: 3.2 mm. Color: 10YR 8/8. Ovary: Shape: Urn. Length: 0.6 cm. Width: 0.6 cm. Color: 10YR 8/8.
*Androecium*.—Stamens: Number: Approximately 50. Position: Below the stigma on the style. Anther: Shape: Round. Diameter: 1.6 mm. Color: 7.5Y 9/12. Filament: Length: 3.2 mm. Width: 1.6 mm. Color: 7.5Y 9/12. Pollen: Color: 7.5Y 9/12. Amount (generally): Abundant.

SEEDS

Seeds: None produced.

I claim:

1. A new and distinct variety of *Hibiscus* plant named 'JBG RH-05', substantially as illustrated and described herein.

* * * * *